United States Patent [19]

Aya et al.

[11] Patent Number: 4,514,210
[45] Date of Patent: * Apr. 30, 1985

[54] HERBICIDALLY ACTIVE METHYL-SUBSTITUTED TETRAHYDRO-2-PYRIMIDINONE DERIVATIVES

[75] Inventors: Masahiro Aya; Junichi Saito; Kazuomi Yasui, all of Tokyo; Kozo Shiokawa, Kanagawa, all of Japan

[73] Assignee: Nihon Tokushu Noyaku Seizo K.K., Tokyo, Japan

[*] Notice: The portion of the term of this patent subsequent to Sep. 6, 2000 has been disclaimed.

[21] Appl. No.: 466,696

[22] Filed: Feb. 15, 1983

[30] Foreign Application Priority Data

Feb. 16, 1982 [JP] Japan .................. 57-22109

[51] Int. Cl.³ .................. C07D 239/10; A01N 43/54
[52] U.S. Cl. .................. 71/92; 544/315; 544/318
[58] Field of Search .................. 544/315, 318; 71/92

[56] References Cited

U.S. PATENT DOCUMENTS 4,063,021 12/1977 Cipriani .................. 548/317
4,402,731 9/1983 Aya .................. 71/92

FOREIGN PATENT DOCUMENTS 58868 9/1982 European Pat. Off. .................. 71/92
1126392 3/1962 Fed. Rep. of Germany .......... 71/92

OTHER PUBLICATIONS

Chemical Abstracts, vol. 57, 1962, pp. 9859–9860.

*Primary Examiner*—Robert Gerstl
*Attorney, Agent, or Firm*—Sprung Horn Kramer & Woods

[57] ABSTRACT

Methyl-substituted tetrahydro-2-pyrimidinone derivatives of the general formula

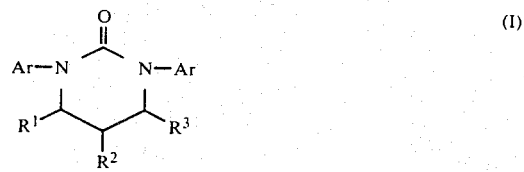

in which
  each Ar, independently of each other, represents an aryl group which is optionally mono- or poly-substituted by substituent(s) selected from halogen, $C_1$ to $C_6$ alkyl, $C_1$ to $C_6$ alkoxy, $C_1$ to $C_6$ alkylthio, nitro, phenoxy and trifluoromethyl, and
  $R^1$, $R^2$ and $R^3$ independently represent a hydrogen atom or a methyl group, provided that at least one of $R^1$, $R^2$ and $R^3$ represents a methyl group, are new and find use as herbicides, in particular as selective herbicides which may be used on weeds in crops such as cotton and rice. The N,N'-diaryl-N-haloalkyl-ureas which are starting materials for the production of compounds of formula (I) are also new.

12 Claims, No Drawings

HERBICIDALLY ACTIVE METHYL-SUBSTITUTED TETRAHYDRO-2-PYRIMIDINONE DERIVATIVES

The present invention relates to certain new methyl-substituted tetrahydro-2-pyrimidinone derivatives, to a process for their production and to their use as herbicides.

The invention also relates to novel intermediates for production of said derivative active compounds of the invention and to a process for producing such intermediates.

The compounds 1-methyl-3-phenylhexahydro-2-pyrimidinone and 1-methyl-3-phenyl-5-methyl-2-imidazolidinone have been disclosed in Chemical Abstracts, Vol. 57, 9860a, 1962; however there is no indication therein of their utility. Tests similar to those described later in this specification show these compounds to have scarcely any herbicidal activity.

The present invention now provides, as new compounds, the methyl-substituted tetrahydro-2-pyrimidinone derivatives of the general formula

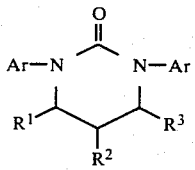
(I)

in which
each Ar, independently of each other, represents an aryl group which is optionally mono- or polysubstituted by substituent(s) selected from halogen, $C_1$ to $C_6$ alkyl, $C_1$ to $C_6$ alkoxy, $C_1$ to $C_6$ alkylthio, nitro, phenoxy and trifluoromethyl, and
$R^1$, $R^2$ and $R^3$ independently represent a hydrogen atom or a methyl group,
provided that at least one of $R^1$, $R^2$ and $R^3$ represents a methyl group.

The present invention further provides a process for the production of a compound of the present invention, characterized in that a compound of the general formula

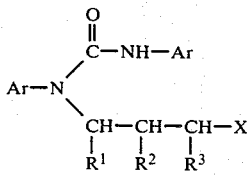
(II)

in which
Ar, $R^1$, $R^2$ and $R^3$ have the meanings given above, and
X represents a halogen atom,
is reacted with an alkali metal hydroxide of the general formula

MOH           (III)

in which M represents an alkali metal atom.

The new methyl-substituted tetrahydro-2-pyrimidinone derivatives of the present invention are distinguished by an excellent selective herbicidal activity.

The present invention further provides as new intermediate compounds, the N,N'-diaryl-N-haloalkylurea of general formula (II) as defined above.

The present invention yet further provides a process for the production of an intermediate compound of formula (II) according to the invention, characterized in that an amine of the general formula

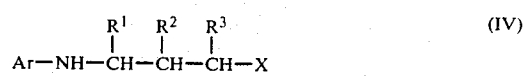
(IV)

in which Ar, $R^1$, $R^2$, $R^3$ and X have the meanings given above,
is reacted with an isocyanate of the general formula

(V)

in which Ar has the meaning given above, and may be the same as or different from the Ar radical in the amine of formula (IV).

It has now been discovered that while the aforesaid known compounds described in the literature scarcely have herbicidal activity as shown by the results of test described hereinafter, the compounds of formula (I) of the present invention surprisingly have excellent selective herbicidal activity and exert an accurate controlling effect on undesired weeds in the cultivation of useful crops such as cotton and rice without any phytotoxicity to the crops. In view of the fact that the compounds of general formula (I) in accordance with this invention cause complete whitening and withering of the stalks and leaves of weeds, the characteristic of the operating mechanism of these compounds is considered to reside mainly in the inhibition of chlorophyll synthesis. Thus the active compounds of the present invention do not affect cotton, rice, and other useful crops, in view of this operating mechanism.

The present invention thus represents an enrichment of the art.

Preferred compounds of formula (I), according to the invention are those
in which
Ar represents a phenyl or α-naphthyl group which is optionally mono- or polysubstituted by substituent(s) selected from: fluorine, chlorine, bromine, iodine, methyl, ethyl, propyl, isopropyl, n-butyl, isobutyl, sec.-butyl, tert.-butyl, methoxy, ethoxy, propoxy, isopropoxy, n-butoxy, isobutoxy, sec.-butoxy, tert.-butoxy, methylthio, ethylthio, propylthio, isopropylthio, n-butylthio, isobutylthio, sec.-butylthio, tert.-butylthio, nitro, phenoxy and trifluoromethyl, and
$R^1$, $R^2$ and $R^3$ have the meanings given above.

Particularly preferred compounds of formula (I) are those in which at least one of the radicals Ar carries a substituent in the meta-position.

The reaction according to the present invention for the production of compounds of formula (I) may be described by the following equation:

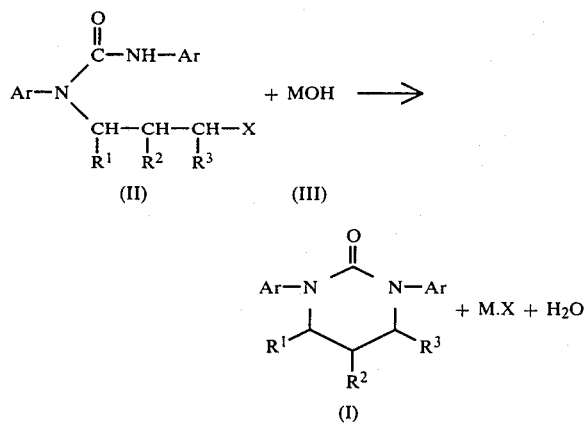

(in which Ar, $R^1$, $R_2$, $R^3$, X and M are as defined hereinabove).

Preferred starting materials of formula (II) are those in which Ar, $R^1$, $R^2$ and $R^3$ have the meanings given in the definition of preferred and particularly preferred compounds of formula (I), and X represents a fluorine, chlorine, bromine or iodine atom.

Examples of compounds of formula (II) which may be mentioned include:
N-[3-chloro or bromo-2-methylpropyl]-N-phenyl-N'-fluoro(or chloro or bromo)phenylurea, N-[3-chloro(or bromo)-2-methylpropyl]-N-3-fluoro(or chloro or bromo)phenyl-N'-phenylurea, N-[3-chloro(or bromo)-2-methylpropyl]-N-phenyl-N'-3-methoxy(or methylthio phenylurea, N-[3chloro(or bromo)-2-methylpropyl]-N-3-methoxy(or methylthio)phenyl-N'-phenylurea, N-[3-chloro(or bromo)-2-methylpropyl]-N-3-nitrophenyl-N'-phenylurea, N-[3chloro(or bromo)-2-methylpropyl]-N-phenyl-N'-3-nitrophenylurea, N-[3-chloro(or bromo)-2-methylpropyl]-N-3-phenoxyphenyl-N'-phenylurea, N-[3-chloro(or bromo)-2-methylpropyl]-N-phenyl-N'-3-phenoxyphenylurea, N-[3chloro(or bromo)-2-methylpropyl]-N-3-trifluoromethylphenyl-N'-phenylurea, N-[3-chloro(or bromo)-2-methylpropyl]-N-phenyl-N'-3-trifluoromethylphenylurea, N-[3-chloro(or bromo)-2-methylpropyl]-N-3,4-dichlorophenyl-N'-phenylurea, N-[3-chloro(or bromo)-2-methylpropyl]-N-phenyl-N'-3,4-dichlorophenylurea, N-[3-chloro(or bromo)-2-methylpropyl]-N-3,5-dichloro(or dimethoxy)phenyl-N'-phenylurea, N-[3-chloro(or bromo)-2-methylpropyl]-N-phenyl-N'-3,5-dichloro(or dimethoxy)phenylurea, N-[3-chloro(or bromo)-2-methylpropyl]-N-α-naphthyl-N'-phenylurea, N-[3-chloro(or bromo)-2-methylpropyl]-N-phenyl-N'-α-naphthylurea, N-[3-chloro(or bromo)-2-methylpropyl]-N-2,4,5-trichlorophenyl-N'-phenylurea, N-[3-chloro(or bromo)-2-methylpropyl]-N-phenyl-N'-2,4,5-trichlorophenylurea, N-[3-chloro(or bromo)-2-methylpropyl]-N-2-chlorphenyl-N'-3-chloro(or trifluoromethyl)phenylurea, N-[3-chloro(or bromo)-2-methylpropyl]-N-3-chloro(or trifluoromethyl)phenyl-N'-2-chlorophenylurea, N-[3-chloro(or bromo)-2-methylpropyl]-N-2-tolyl-N'-3-chloro(or methylthio or trifluoromethyl)phenylurea, N-[3-chloro(or bromo)-2-methylpropyl]-N-3-chloro(or methylthio or trifluoromethyl)phenyl-N'-2-tolylurea, N-[3-chloro(or bromo)-2-methylpropyl]-N-3,5-xylyl-N'-phenylurea, N-[3-chloro(or bromo)-2-methylpropyl]-N-phenyl-N'-3,5-xylylurea, N-[3-chloro(or bromo)-2-methylpropyl]-N-2-methoxyphenyl-N'-3-chloro(or methylthio or trifluoromethyl)phenylurea, N-[3-chloro(or bromo)-2-methylpropyl]-N-3-chloro(or methylthio or trifluoromethyl)phenyl-N'-2-methoxyphenylurea, N-[3-chloro(or bromo)-2-methylpropyl]-N-3-tolyl-N'-2-methoxyphenylurea, N-[3-chloro(or bromo)-2-methylpropyl]-N-2-methoxyphenyl-N'-3-tolylurea, N-[3-chloro(or bromo)-2-methylpropyl]-N-3-chlorophenyl-N'-3-chloro(or trifluoromethyl)phenylurea, N-[3-chloro(or bromo)-2-methylpropyl]-N-3-chloro(or trifluoromethyl)phenyl-N'-3-chlorophenylurea, N-[3-chloro(or bromo)-2-methylpropyl]-N-3-tolyl-N'-3-chlorophenylurea, N-[3-chloro(or bromo)-2-methylpropyl]-N-3-chlorophenyl-N'-3-tolylurea, N-[3-chloro(or bromo)-2-methylpropyl]-N-2-methoxyphenyl-N'-3,4-dichloro(or 3,5-dichloro)phenylurea, N-[3-chloro(or bromo)-2-methylpropyl]-N-3,4-dichloro(or 3,5-dichloro)phenyl-N'-2-methoxyphenylurea, N-[3-chloro(or bromo)-2-methylpropyl]-N-2-tolyl-N'-3,5-dichlorophenylurea, N-[3-chloro(or bromo)-2-methylpropyl]-N-3,5-dichlorophenyl-N'-2-tolylurea, N-[3-chloro(or bromo)-1-methyl(or 3-methyl)-propyl]-N-phenyl-N'-3-chloro(or trifluoromethyl)phenylurea, N-[3-chloro(or bromo)-1-methyl(or 3-methyl)propyl]-N-3-chloro(or trifluoromethyl)phenyl-N'-phenylurea, N-[3-chloro(or bromo)-1-methyl(or 3-methyl)propyl]-N-phenyl-N'-3,5-dichlorophenylurea, and N-[3-chloro(or bromo)-1-methyl(or 3-methyl)-propyl]-N-3,5-dichlorophenyl-N'-phenylurea.

Preferred alkali metal hydroxides of general formula (III) which are also starting materials in the reaction for the production of compounds of formula (I) are lithium hydroxide, sodium hydroxide and potassium hydroxide.

If the starting materials indicated are used, the process for the production of compounds of formula (I) is illustrated by the following equation:

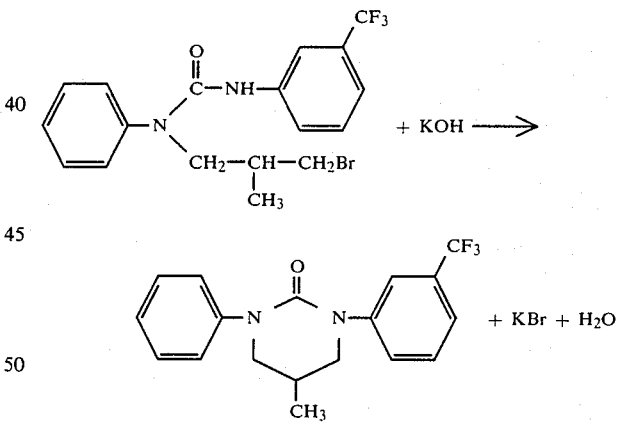

The process for the preparation of the compounds of formula (I) according to the present invention is preferably carried out in the presence of a solvent or a diluent. For this purpose, any of the inert solvents and diluents may be employed. These include in particular water, aliphatic, alicyclic and aromatic, optionally chlorinated, hydrocarbons (such as hexane, cyclohexane, petroleum ether, ligroin, benzene, toluene, xylene, methylene chloride, chloroform, carbon tetrachloride, ethylene chloride, trichloroethylene and chlorobenzene), ethers (such as diethyl ether, methyl ethyl ether, diisopropyl ether, dibutyl ether, propylene oxide, dioxane and tetrahydrofuran), ketones (such as acetone, methyl ethyl ketone, methyl isopropyl ketone and methyl isobutyl ketone), nitriles (such as acetonitrile, propionitrile and acrylonitrile), alcohols (such as methanol, ethanol, isopropanol, butanol and ethylene glycol), esters (such as ethyl acetate and amyl acetate), acid amides (such as dimethyl formamide and dimethyl acetamide), sulfones and sulfoxides (such as dimethyl sulfoxide and sulfolane) and bases (such as pyridine).

The reaction temperature can be varied within a substantial range. In general, the reaction is carried out at a temperature between $-20°$ C. and the boiling point of the reaction mixture, preferably between 0° and 100° C.

The process according to the present invention is preferably carried out under ambient pressure, although it can be carried out under elevated or reduced pressure.

As mentioned previously, the N,N'-diaryl-N-haloalkylureas of the formula (II) above are novel compounds which form a further subject of the present invention and are useful as intermediates for the methyl-substituted tetrahydro-2-pyrimidinone derivatives of the formula (I), above, which, as described above, have excellent selective herbicidal activity.

The further process according to the present invention for the production of starting compounds of formula (II) is indicated by the following equation:

$$Ar-NH-\overset{R^1}{\underset{}{\overset{|}{C}H}}-\overset{R^2}{\underset{}{\overset{|}{C}H}}-\overset{R^3}{\underset{}{\overset{|}{C}H}}-X + Ar-N=C=O \longrightarrow$$
(IV)           (V)

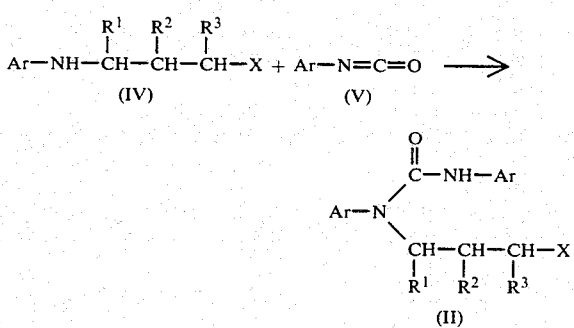

(in which Ar, $R^1$, $R^2$, $R^3$ and X are as defined hereinabove).

Examples of the starting material of general formula (IV) which may be mentioned include:

N-[3-chloro(or bromo)-2-methylpropyl]aniline, N-[3-chloro(or bromo)-2-methylpropyl]-3-fluoro(or chloro or bromo)aniline, N-[3-chloro(or bromo)-2-methylpropyl]-3-methoxy(or methylthio) aniline, N-[3-chloro(or bromo)-2-methylpropyl]-3-nitroaniline, N-[3-chloro(or bromo)-2-methylpropyl]-3-phenoxyaniline, N-[3-chloro(or bromo)-2-methylpropyl]-3-trifluoromethylaniline, N-[3-chloro(or bromo)-2-methylpropyl]-3,4-dichloroaniline, N-[3-chloro(or bromo)-2-methylpropyl]-3,5-dichloro(or dimethoxy)aniline, N-[3-chloro(or bromo)-2-methypropyl]-α-naphthylamide, N-[3-chloro(or bromo)-2-methylpropyl]-2,4,5-trichloroaniline, N-[3-chloro(or bromo)-2-methylpropyl]-2-chloroaniline, N-[3-chloro(or bromo)-2-methylpropyl]-2-toluidine, N-[3-chloro(or bromo)-2-methylpropyl]-2-methoxyaniline, N-[3-chloro(or bromo)-2-methylpropyl]-3-toluidine, N-[3-chloro(or bromo)-1-methyl(or 3-methyl)propyl]aniline, N-[3-chloro(or bromo)-1-methyl(or 3-methyl)propyl]-3-chloro(or trifluoromethyl)aniline, N-[3-chloro(or bromo)-2-methylpropyl]-3,5-xylidine, and N-[3-chloro(or bromo)-1-methyl(or 3-methyl)propyl]-3,5-dichloroaniline.

Likewise, specific examples of the starting isocyanate of general formula (V) include:

phenyl isocyanate, 3-fluoro(or chloro or bromo)phenyl isocyanate, 3-methoxy(or methylthio)phenyl isocyanate, 3-nitrophenyl isocyanate, 3-phenoxyphenyl isocyanate, 3-trifluoromethylphenyl isocyanate, 3,4-dichlorophenyl isocyanate, 3,5-dichlorophenyl isocyanate, 3,5-xylyl isocyanate, α-naphthyl isocyanate, 3,5-dimethoxyphenyl isocyanate, 2,4,5-trichlorophenyl isocyanate, 2-chlorophenyl isocyanate, 2-tolyl isocyanate, 2-methoxy isocyanate, and 3-tolyl isocyanate.

If the starting materials indicated are used, the process according to the invention for the production of compounds of formula (III) is illustrated by the following equation:

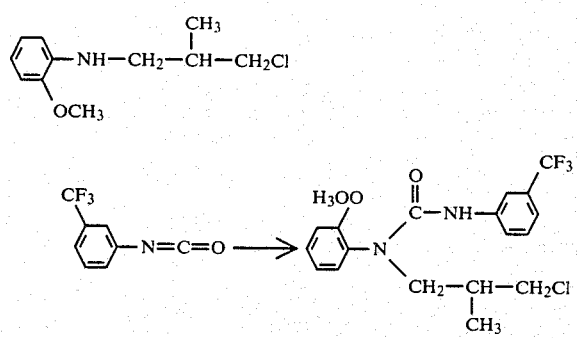

The process according to the invention for the production of compounds of formula (II) is preferably carried out in the presence of a solvent or diluent. Any of those inert solvents or diluents mentioned above for the production of compounds of formula (I) can be used.

The reaction temperature can be caried out with a substantial range. In general the reaction is carried out at a temperature between $-20°$ C. and the boiling point of the reaction mixture, preferably between 0° and 100° C.

The reaction for the production of compounds of formula (II) is preferably carried out under ambient pressure, but it is also possible to operate under elevated or reduced pressures.

In a preferred embodiment of the process according to the invention, the methyl-substituted tetrahydropyrimidinone derivatives of general formula (I) can be produced in high yields and purities using the starting materials of formula (II) obtained from the compounds of general formulae (IV) and (V) in the process for producing the aforesaid intermediates without intermediate separation of the compounds of formula (II).

This embodiment is shown in the following equation:

$$Ar-NH-\overset{R^1}{\underset{}{\overset{|}{C}H}}-\overset{R^2}{\underset{}{\overset{|}{C}H}}-\overset{R^3}{\underset{}{\overset{|}{C}H}}-X + Ar-N=C=O \longrightarrow$$
(IV)           (V)

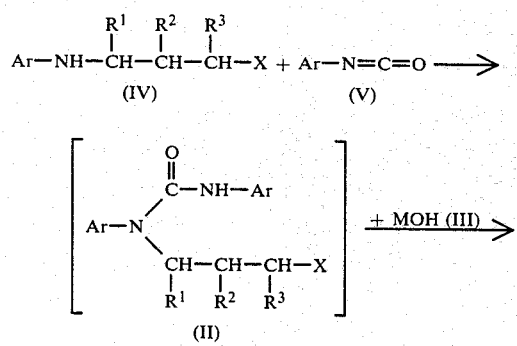

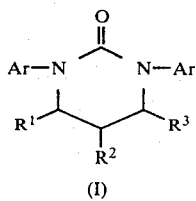

(in which Ar, $R^1$, $R^2$ and $R^3$ and X are as defined hereinabove).

If the starting materials indicated are used, this embodiment is illustrated further by the following equation:

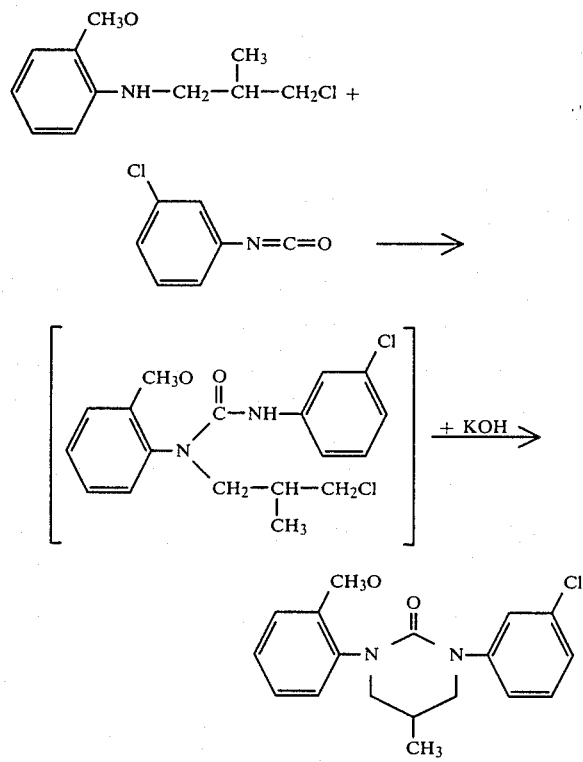

The embodiment is carried out using the same inert solvent or diluents as those mentioned above and can be carried out efficiently in the presence of a catalyst such as tetrabutyl ammonium bromide. The temperatures and pressures employed in this embodiment are also as indicated previously.

Since the compounds of formula (I) according to the present invention exhibit low toxicity to warm-blooded animals and the aforesaid excellent selectivity, the said compounds are very suitable for weed control. In particular, the compounds of formula (I) of the invention exhibit a very good selectivity to crops with outstanding efficacy for weed control when used as pre-emergence and post-emergence treatment agents in the cultivation of cotton and rice. The compounds of formula (I) of the invention have a high safety to the crops and outstanding herbicidal activity, and a broad herbicidal spectrum.

By "weeds" in the broadest sense there are meant plants growing in places where they are not desired.

The active compounds according to the present invention are excellent with regard to their safety, manifest a superior herbicidal activity and have wide herbicidal spectra.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Spenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the present invention show a superior selective control effect. For example they show herbicidal activity on weeds in paddy rice fields such as those listed below without showing any harmful effect on rice plants:

the dicotyledon weeds *Rotala indica Koehne, Lindernia Procumbens Philcox, Ludwigia prostrata Roxburgh, Potamogeton distinctus A. Benn* and *Elatine triandra Schk;* and the monocotyledon weeds *Echinochloa crus-galli P. Beaur.* var., *Monochoria vaginalis Presl., Eleocharis acicularis L., Eleocharis Kuroguwai Ohwi, Cyperus diffornis L. Cyprus serotinus Rottboel, Sagittaria pygmaea Miq., Alisma canaliculatum A. Br. et Bouche* and *Scirpus juncoides Roxburgh* var.

The applicability of the active compounds of formula (I) of the invention is not limited to weeds in aquatic paddies and upland farms. They are also effective against weeds noxious in mat rush (*Juncus effusus Linnaeus* var. *decipiens Buchanan*) and weeds occurring in lands which are temporarily out of cultivation.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.001 to 100 percent by weight of active compound, preferably from 0.005 to 95 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They are preferably applied before emergence of the plants, that is to say by the pre-emergence method. They can also be incorporated into the soil before sowing.

Further, it is also possible to apply the active compounds by means of the ultra-low-volume method, whereby it is possible to employ the compounds at a concentration of up to 100% by weight.

In actual use, the content of the active ingredients in the various preparations and ready-to-use preparations is generally in the range of 0.01 to 95% by weight, preferably 0.05 to 60% by weight.

The dosage of the active compound per unit area is generally 0.5 to 5.0 kg, preferably 1.0 to 4.0 kg, per hectare. In special cases, however, it is possible, or sometimes even necessary, to employ a dosage higher or lower than the above range.

The present invention also provides herbicidal compositions containing as active ingredient a compound of the present invention in admixture with a solid diluent or carrier or in admixture with a liquid diluent or carrier containing a surface-active agent.

The present invention also provides a method of combating weeds which comprises applying to the weeds or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

Compositions according to the invention are illustrated by the following Examples (i) to (vi). In these Examples, the compounds according to the invention are each identified by the number (given in brackets) of the corresponding preparative example.

Example (i)

15 Parts by weight of compound (1), 80 parts by weight of a 1:5 mixture of powdery diatomaceous earth and powder clay, 2 parts by weight of sodium alkylbenzenesulfonate, and 3 parts of a sodium alkylnaphthaleneusulfonate/formaldehyde condensate were pulverized and mixed to form a wettable powder. It was diluted with water before spraying.

Example (ii)

30 Parts by weight of compound (2), 55 parts by weight of xylene, 8 parts by weight of polyoxyethylene alkyl phenyl ether and 7 parts by weight of calcium alkylbenzenesulfonate were mixed with stirring to form an emulsifiable concentrate. It was diluted with water before spraying.

Example (iii)

2 Parts by weight of compound (3) and 98 parts of powdery clay were pulverized and mixed to form a dusting agent.

Example (iv)

1.15 Parts by weight of compound (4), 0.5 parts by weight of isopropyl hydrogen phosphate, and 98 parts by weight of powdery clay were pulverized and mixed to form a dusting agent.

Example (v)

25 Parts by weight of water was added to a mixture consisting of 10 parts by weight of compound (5), 30 parts by weight of bentonite (montmorillonite), 58 parts by weight of talc and 2 parts by weight of a lignosulfonate, and there were well kneaded. The mixture was processed by an extrusion-type granulating machine to form granules having a size of 10 to 40 mesh which were then dried at 40° to 50° C. to prepare granules. They were applied by scattering.

Example (vi)

95 Parts by weight of clay mineral particles having a particle size distribution between 0.2 and 2 mm were put in a rotary mixer, and with rotation, 5 parts by weight of compound (7) dissolved in an organic solvent was sprayed onto the particles to wet them equally. The particles were then dried at 40° to 50° C. to form granules. The granules were applied by scattering.

The herbicidal activity of the compounds of this invention is illustrated by the following biotest examples.

In these examples the compounds according to the present invention are each identified by the number (given in brackets) of the corresponding preparative example.

The known comparison compounds described in Chemical Abstracts, Vol. 57, 9860a 1962 are identified as follows:

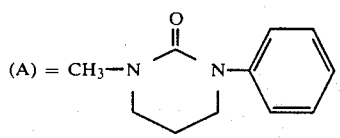

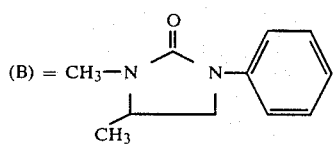

Example A

Test for determining a herbicidal effect on upland farm weeds (pot test):

Solvent: 5 parts by weight of acetone Emulsifier: 1 part by weight of benzyloxy polyglycol ether To produce a suitable preparation of active compound, 1 part by weight of the active compound was mixed with the stated amount of solvent, the stated amount of emulsifier was added and the concentrate was diluted with water to the desired concentration.

Plastic pots (1/2000 ares; 25 cm×20 cm×10 cm) were each filled with 2.5 liters of alluvial soil screened with a screen having a mesh opening size of 0.5 cm×0.5 cm. Seeds of cotton (variety: coker 310) were sown in the soil to a depth of 1 cm, and the same alluvial soil as above containing seeds of *Digitaria adscendens Henr., Echinochloa crus-galli, Amaranthus retroflexus L., Chenopodium album Linnaeus,* and *Portulaca oleracea Linnaeus,* were put over the soil in the pot. The preparation of the chemical was uniformly sprayed on the surface layer of each test pot at a predetermined dosage. The herbicidal effect was examined 20 days after the treatment, and the degree of phytotoxicity was examined 20 days, 40 days and 60 days respectively after the treatment. The results were rated in scores of 0 to 10 according to the following criterion:

The evaluation of the effect is expressed in the following rating 0 to 10 according to the weed killing rate relative to that in the non-treated area.

| Rating | Weed-kill ratio based on the control |
| --- | --- |
| 10: | 100% (completely withered) |
| 9: | 90 to less than 100% |
| 8: | 80% to less than 90% |
| 7: | 70% to less than 80% |
| 6: | 60% to less than 70% |
| 5: | 50% to less than 60% |
| 4: | 40% to less than 50% |
| 3: | 30% to less than 40% |
| 2: | 20% to less than 30% |
| 1: | 10% to less than 20% |
| 0: | less than 10% (no herbicidal effect) |

The evaluation of the phytotoxicity to cotton plants is expressed in the following rating 0 to 10 according to the phytotoxicity relative to that in the non-treated area.

| Rating | Phytotoxicity rate in comparison with the control |
| --- | --- |
| 10: | at least 90% (fatal injury) |
| 9: | 80% to less than 90% |
| 8: | 70% to less than 80% |
| 7: | 60% to less than 70% |
| 6: | 50% to less than 60% |
| 5: | 40% to less than 50% |
| 4: | 30% to less than 40% |
| 3: | 20% to less than 30% |
| 2: | 10% to less than 20% |
| 1: | more than 0 but less than 10% |
| 0: | 0% (no phytotoxicity) |

The test results are given in Table 1.

TABLE 1

| Compound No. | Amount of the active ingredient (kg/ha) | Herbicidal effect Weed | | | | | Phytotoxicity cotton | | |
|---|---|---|---|---|---|---|---|---|---|
| | | D. adscendens | E. Crus-galli | A. retroflexus | C. album | P. oberacea | 20 days | 40 days | 60 days |
| (1) | 4.0 | 10 | 10 | 10 | 10 | 10 | 0 | 0 | 0 |
| (2) | 4.0 | 10 | 10 | 10 | 10 | 10 | 0 | 0 | 0 |
| (3) | 4.0 | 10 | 10 | 10 | 10 | 10 | 0 | 0 | 0 |
| (4) | 4.0 | 10 | 10 | 10 | 10 | 10 | 0 | 0 | 0 |
| (5) | 4.0 | 10 | 10 | 10 | 10 | 10 | 0 | 0 | 0 |
| (6) | 4.0 | 10 | 10 | 10 | 10 | 10 | 0 | 0 | 0 |
| (7) | 4.0 | 10 | 10 | 10 | 10 | 10 | 0 | 0 | 0 |
| (8) | 4.0 | 10 | 10 | 10 | 10 | 10 | 0 | 0 | 0 |
| (9) | 4.0 | 10 | 10 | 10 | 10 | 10 | 0 | 0 | 0 |
| (10) | 4.0 | 10 | 10 | 10 | 10 | 10 | 0 | 0 | 0 |
| (11) | 4.0 | 10 | 10 | 10 | 10 | 10 | 0 | 0 | 0 |
| (12) | 4.0 | 10 | 10 | 10 | 10 | 10 | 0 | 0 | 0 |
| (13) | 4.0 | 10 | 10 | 10 | 10 | 10 | 0 | 0 | 0 |
| (14) | 4.0 | 10 | 10 | 10 | 10 | 10 | 0 | 0 | 0 |
| (15) | 4.0 | 10 | 10 | 10 | 10 | 10 | 0 | 0 | 0 |
| (16) | 4.0 | 10 | 10 | 10 | 10 | 10 | 0 | 0 | 0 |
| (17) | 4.0 | 10 | 10 | 10 | 10 | 10 | 0 | 0 | 0 |
| (18) | 4.0 | 10 | 10 | 10 | 10 | 10 | 0 | 0 | 0 |
| (19) | 4.0 | 10 | 10 | 10 | 10 | 10 | 0 | 0 | 0 |
| (20) | 4.0 | 10 | 10 | 10 | 10 | 10 | 0 | 0 | 0 |
| (21) | 4.0 | 10 | 10 | 10 | 10 | 10 | 0 | 0 | 0 |
| (22) | 4.0 | 10 | 10 | 10 | 10 | 10 | 0 | 0 | 0 |
| (23) | 4.0 | 10 | 10 | 10 | 10 | 10 | 0 | 0 | 0 |
| (24) | 4.0 | 10 | 10 | 10 | 10 | 10 | 0 | 0 | 0 |
| (25) | 4.0 | 10 | 10 | 10 | 10 | 10 | 0 | 0 | 0 |
| (26) | 4.0 | 10 | 10 | 10 | 10 | 10 | 0 | 0 | 0 |
| (27) | 4.0 | 10 | 10 | 10 | 10 | 10 | 0 | 0 | 0 |
| (28) | 4.0 | 10 | 10 | 10 | 10 | 10 | 0 | 0 | 0 |
| (29) | 4.0 | 10 | 10 | 10 | 10 | 10 | 0 | 0 | 0 |
| (30) | 4.0 | 10 | 10 | 10 | 10 | 10 | 0 | 0 | 0 |
| Comparison | | | | | | | | | |
| (A) | 4.0 | 1 | 1 | 0 | 0 | 1 | 0 | 0 | 0 |
| (B) | 4.0 | 0 | 0 | 0 | 0 | 0 | 0 | 0 | 0 |

Example B

Test of stalk and filiar treatment and soil treatment of aquatic paddy weeds in a submerged condition (pot test)

Paddy soil was filled in Wagner pots (1/5000 ares), and two 2- to 3-leaf stage (height about 10 cm) rice seedlings (variety: Kinnampu) were transplanted per pot. Seeds of broad-leaved weeds, Echinochloa crus-galli, Cyperus sp., Monochoria vaginalis Presl and Scirpus juncoides Roxburgh var., were sown, and small fragments of Eleocharis acicularis L., and tubers of Cyperus serotinus Rottboel and Sagittaria pygmaea Miq. were buried in the soil. The pots were each maintained in a wet condition. When seeds of Echinochloa crus-galli grew to a stage of about 2 leaves (about 7 to 9 days after the sowing), the soil in the pot was flooded to a water depth of about 6 cm. Each of the preparations of active compound prepared in the same way as in Example A was applied by means of a pippette. After the treatment, the water was allowed to leak for two days from the pot at a rate of 2 to 3 cm per day. Thereafter, the pots were each flooded to a water depth of about 3 cm. In the fourth week after the treatment with the chemical, the herbicidal effects and degrees phytotoxicity of the chemicals were evaluated on a scale of 0 to 10 in the same way as in Example A. The results are shown in following Table 2.

TABLE 2

| Component | Amount of the active ingredient (kg/ha) | Herbicidal Effect Weed | | | | | | | | Phytotoxicity Rice |
|---|---|---|---|---|---|---|---|---|---|---|
| | | A | B | C | D | E | F | G | H | |
| (6) | 2.0 | 10 | 10 | 10 | 10 | 10 | 10 | 10 | 10 | 0 |
| (17) | 2.0 | 10 | 10 | 10 | 10 | 10 | 10 | 10 | 10 | 0 |
| Comparison | | | | | | | | | | |
| (A) | 4.0 | 1 | 0 | 1 | 0 | 1 | 3 | 0 | 2 | 0 |
| (B) | 4.0 | 1 | 0 | 0 | 0 | 0 | 0 | 0 | 0 | 0 |

Note: A, B, C, D, E, F, G and H in the column of "Weed" of Table 2 stand for the following weeds.
- A: Echinochloa crus-galli
- B: Eleocharis acicularis
- C: Cyperus sp.
- D: Scirpus juncoides
- E: Monochoria vaginalis
- F: Broad-leaved weeds (such as Lindernia procumbens, Rotala indica and Elatine triandra)
- G: Cyperus serotinus
- H: Sagittaria pygmaea The following Examples 1 to 30 illustrate the production of the methyl-substituted tetrahydro-2-pyrimidinone derivative of general formula (I) of the invention, while Examples 31 to 62 illustrate the production of the novel intermediates of formula (II) according to the invention.

Preparative Examples

Example 1

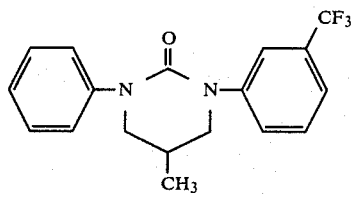

(1)

37 g of N-(3-chloro-2-methylpropyl)-N-phenyl-N'-3-trifluoromethylphenylurea was dissolved in 150 ml of ethanol, and 56 g of a 20% by weight ethanolic solution of potassium hydroxide was added. They reacted exothermically. To complete the reaction, the mixture was stirred under reflux for 2 hours. Then the ethanol was distilled off under reduced pressure, and water was added to the residue. The desired product precipitated as crystals. Recrystallization from methanol gave 27 g of the desired 5-methyl-1-phenyl-3-(3-trifluoromethylphenyl)-tetrahydro-2-pyrimidinone as colorless crystals. mp. 121° to 123° C.

Example 2

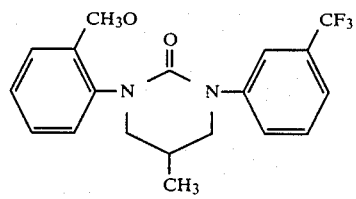

(2)

40 g of N-(3-chloro-2-methylpropyl)-N-2-methoxyphenyl-N'-3-trifluoromethylphenylurea was dissolved in 150 ml of isopropanol, and 20 g of a 50% by weight aqueous solution of sodium hydroxide was added to the solution at 30° to 35° C. while stirring well. The reaction mixture was then stirred at 65° to 75° C. for 2 hours, and the isopropanol was distilled off under reduced pressure. 100 ml of toluene was added to the residue and the mixture was washed with 1% by weight HCl and then with water. After dehydration, the toluene was distilled off under reduced pressure to give 26.6 g of the desired 1-(2-methoxyphenyl)-5-methyl-3-(3-trifluoromethylphenyl)-tetrahydro-2-pyrimidinone as a viscous pale yellow liquid. $n_D^{19}$ 1.5398.

The compounds of the following Examples 3 to 5 were prepared substantially as described in foregoing Examples 1 and 2:

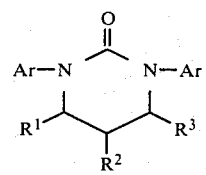

| Example No | Ar | $R^1$ | $R^2$ | $R^3$ | Melting point (°C.)/refractive index ($n_D^{20}$) |
|---|---|---|---|---|---|
| 3 | phenyl | 3-chlorophenyl | H | —CH$_3$ | H | 124–126 |
| 4 | 2-chlorophenyl | 3-chlorophenyl | H | —CH$_3$ | H | 1.5936 |
| 5 | 2-chlorophenyl | 3-trifluoromethylphenyl | H | —CH$_3$ | H | 61–64 |

Example 6

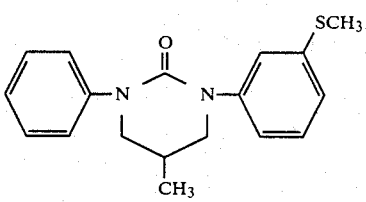

(6)

18.4 g of N-(3-chloro-2-methylpropyl)aniline was dissolved in 120 ml of toluene, and 16.5 g of 3-methylthiophenyl isocyanate was added at room temperature. Then, the mixture was stirred at 40° to 50° C. for 1 hour. A catalytic amount (0.2 g) of tetrabutyl ammonium bromide was then added. While maintaining the temperature of the mixture at 30° to 40° C., 34 g of a 50% by weight aqueous solution of potassium hydroxide was added dropwise to the mixture. After the addition, the mixture was well stirred at 40° to 50° C. for 1 hour to complete the reaction. The reaction mixture was cooled to room temperature. The toluene layer was separated and washed with 1% by weight HCl and water in this order. After dehydration, the toluene was distilled off under reduced pressure to give 20.3 g of the desired 5-methyl-1-(3-methylthiophenyl)-3-phenyl-tetrahydro-2-pyrimidinone as a viscous pale yellow liquid. $n_D^{20}$ 1.6194

The compounds of following Examples 7 to 30 were prepared substantially as described in foregoing Example 6:

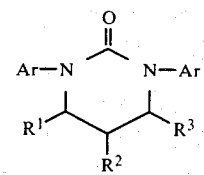
| Example No. | Ar | Ar | $R^1$ | $R^2$ | $R^3$ | Melting point (°C.)/ Refractive index |
|---|---|---|---|---|---|---|
| 7 | phenyl | 3-F-phenyl | H | —CH₃ | H | 99–101 |
| 8 | " | 3-Br-phenyl | H | —CH₃ | H | 118–121 |
| 9 | " | 3-NO₂-phenyl | H | —CH₃ | H | 106–108 |
| 10 | " | 3-phenoxyphenyl | H | —CH₃ | H | $n_D^{19}$ 1.6045 |
| 11 | " | 3,4-diCl-phenyl | H | —CH₃ | H | 116.5–118.5 |
| 12 | " | 3,5-diCl-phenyl | H | —CH₃ | H | 122–125 |
| 13 | " | 3,5-diCH₃-phenyl | H | —CH₃ | H | $n_D^{20}$ 1.5849 |
| 14 | " | 3,5-di(CH₃O)-phenyl | H | —CH₃ | H | $n_D^{19}$ 1.5863 |

-continued
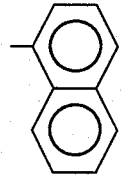
| Example No. | Ar | | R¹ | R² | R³ | Melting point (°C.)/ Refractive index |
|---|---|---|---|---|---|---|
| 15 | " | 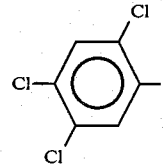 | H | —CH₃ | H | $n_D^{20}$ 1.6266 |
| 16 | " | 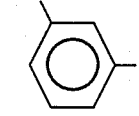 | H | —CH₃ | H | 141–143 |
| 17 | " | 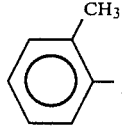 | H | —CH₃ | H | 94–97 |
| 18 | 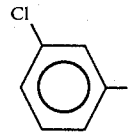 | 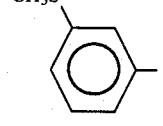 | H | —CH₃ | H | $n_D^{20}$ 1.5900 |
| 19 | " | 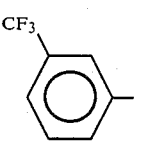 | H | —CH₃ | H | $n_D^{20}$ 1.5976 |
| 20 | " | 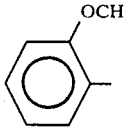 | H | —CH₃ | H | 141.5–143 |
| 21 | 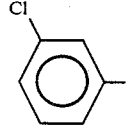 | 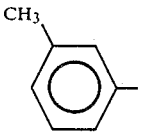 | H | —CH₃ | H | 91–93 |
| 22 | " | 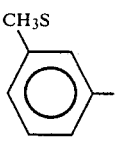 | H | —CH₃ | H | 104–106 |
| 23 | " |  | H | —CH₃ | H | $n_D^{20}$ 1.6125 |

-continued
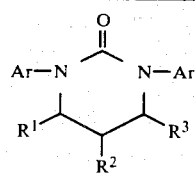
| Example No. | Ar | | R¹ | R² | R³ | Melting point (°C.)/ Refractive index |
|---|---|---|---|---|---|---|
| 24 | 3-Cl-phenyl | 3-Cl-phenyl | H | —CH₃ | H | 155–158 |
| 25 | 2-CH₃-phenyl | 3,5-di-Cl-phenyl | H | —CH₃ | H | 141.5–143.5 |
| 26 | 2-OCH₃-phenyl | 3,4-di-Cl-phenyl | H | —CH₃ | H | $n_D^{19}$ 1.5861 |
| 27 | " | 3,5-di-Cl-phenyl | H | —CH₃ | H | 156–157 |
| 28 | phenyl | 3-Cl-phenyl | —CH₃ | H | H | 93–95 |
| 29 | " | 3-CF₃-phenyl | —CH₃ | H | H | 98–100 |
| 30 | " | 3,5-di-Cl-phenyl | —CH₃ | H | H | 106.5–109.5 |

Preparation of Intermediate Compounds of formula (II)

Example 31

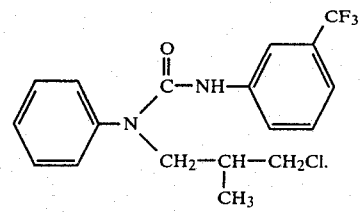

At room temperature, 18.7 g of 3-trifluoromethylphenyl isocyanate was added to a solution of 18.4 g of N-(3-chloro-2-methylpropyl)aniline in 100 ml of chloroform. The mixture was then stirred at 40° C. for 1 hour. When the chloroform was removed under reduced pressure, 37 g of N-[3-chloro-2-methylpropyl]-N-phenyl-N'-3-trifluoromethylphenylurea was obtained. The melting point of the product was 72° to 75° C.

The N,N'-diaryl-N-haloalkylureas of the following Examples 32 to 36 were prepared substantially as described in foregoing Example 31.

| Example No. | Compound | Melting point (°C.)/ Refractive index $n_D^{20}$ |
|---|---|---|
| 32 | N—(3-chloro-2-methylpropyl)-N—phenyl-N'—3-chlorophenylurea | 99–101 |
| 33 | N—(3-chloro-2-methylpropyl)-N—2-methoxyphenyl-N'—3-trifluoromethylphenylurea | 1.5343 |
| 34 | N—(3-chloro-2-methylpropyl)-N—phenyl-N'—3-methylthiophenylurea | 1.5974 |
| 35 | N—(3-chloro-2-methylpropyl)-N—2-chlorophenyl-N'—3-chlorophenylurea | 1.5681 |
| 36 | N—(3-chloro-2-methylpropyl)-N—2-chlorophenyl-N'—3-trifluoromethylphenylurea | 1.5331 |

The N,N'-diaryl-N'-haloalkylureas indicated in the following Examples 37 to 62 were likewise prepared, using the specified starting materials by the process substantially as described in foregoing Example 31:

| Example No. | Starting material | Starting material | Product |
|---|---|---|---|
| 37 | N—(3-chloro-2-methylpropyl)-3-fluoroaniline | Phenyl isocyanate | N—(3-chloro-2-methylpropyl)-N—3-fluorophenyl-N'—phenylurea |
| 38 | N—(3-chloro-2-methylpropyl)-3-bromoaniline | Phenyl isocyanate | N—(3-chloro-2-methylpropyl)-N—3-bromophenyl-N'—phenylurea |
| 39 | N—(3-bromo-2-methylpropyl)-3-bromoaniline | Phenyl isocyanate | N—(3-bromo-3-methylpropyl)-N—3-nitrophenyl-N'—phenylurea |
| 40 | N—(3-bromo-2-methylpropyl)-aniline | 3-Phenoxyphenyl isocyanate | N—(3-bromo-2-methylpropyl)-N—phenyl-N'—3-phenoxyphenylurea |
| 41 | N—(3-bromo-2-methylpropyl)-3,4-dichloroaniline | Phenyl isocyanate | N—(3-bromo-2-methylpropyl)-N—3,4-dichlorophenyl-N'—phenylurea |
| 42 | N—(3-chloro-2-methylpropyl)-aniline | 3,5-Dichlorophenyl isocyanate | N—(3-chloro-2-methylpropyl)-N—phenyl-N'—3,5-dichlorophenylurea |
| 43 | N—(3-chloro-2-methylpropyl)-aniline | 3,5-xylyl isocyanate | N—(3-chloro-2-methylpropyl)-N—phenyl-N'—3,5-xylylurea |
| 44 | N—(3-bromo-2-methylpropyl)-aniline | 3,5-Dimethoxyphenyl isocyanate | N—(3-bromo-2-methylpropyl)-N—phenyl-N'—3,5-dimethoxyphenylurea |
| 45 | N—(3-chloro-2-methylpropyl)-α-naphthylamine | Phenyl isocyanate | N—(3-chloro-2-methylpropyl)-N—α-naphthyl-N'—phenylurea |
| 46 | N—(3-bromo-2-methylpropyl)-2,4,5-trichloroaniline | Phenyl isocyanate | N—(3-bromo-2-methylpropyl)-N—2,4,5-trichlorophenyl-N'—phenylurea |
| 47 | N—(3-chloro-2-methylpropyl)-aniline | 3-Methoxyphenyl isocyanate | N—(3-chloro-2-methylpropyl)-N—phenyl-N'—3-methoxyphenylurea |
| 48 | N—(3-bromo-2-methylpropyl)-2-toluidine | 3-Chlorophenyl isocyanate | N—(3-bromo-2-methylpropyl)-N—2-tolyl-N'—3-chlorophenylurea |
| 49 | N—(3-chloro-2-methylpropyl)-2-toluidine | 3-Methylthiophenyl isocyanate | N—(3-chloro-2-methylpropyl)-N—2-tolyl-N'—3-methylthiophenylurea |
| 50 | N—(3-chloro-2-methylpropyl)-2-toluidine | 3-Trifluoromethylphenyl isocyanate | N—(3-chloro-2-methylpropyl)-N—2-tolyl-N'—3-trifluoromethylphenylurea |
| 51 | N—(3-chloro-2-methylpropyl)-2-methoxyaniline | 3-Chlorophenyl isocyanate | N—(3-chloro-2-methylpropyl)-N—2-methoxyphenyl-N'—3-chlorophenylurea |
| 52 | N—(3-chloro-2-methylpropyl)-2-methoxyaniline | 3-Tolylisocyanate | N—(3-chloro-2-methylpropyl)-N—2-methoxyphenyl-N'—3-tolylurea |
| 53 | N—(3-bromo-2-methylpropyl)-2-methoxyaniline | 3-Methylthiophenyl isocyanate | N—(3-bromo-2-methylpropyl)-N—2-methoxyphenyl-N'—3-methylthiophenylurea |
| 54 | N—(3-chloro-2-methylpropyl)-3-chloroaniline | 3-Chlorophenyl isocyanate | N—(3-chloro-2-methylpropyl)-N,N'—bis-(3-chlorophenyl)-urea |

-continued

| Example No. | Starting material | Starting material | Product |
|---|---|---|---|
| 55 | N—(3-bromo-2-methylpropyl)-2-toluidine | 3,5-Dichlorophenyl isocyanate | N—(3-bromo-2-methylpropyl)-N—2-tolyl-N'—3,5-dichlorophenylurea |
| 56 | N—(3-bromo-2-methylpropyl)-2-methoxyaniline | 3,4-Dichlorophenyl isocyanate | N—(3-bromo-2-methylpropyl)-N—2-methoxyphenyl-N'—3,4-dichlorophenylurea |
| 57 | N—(3-chloro-2-methylpropyl)-2-methoxyaniline | 3,5-Dichlorophenyl isocyanate | N—(3-chloro-2-methylpropyl)-N—2-methoxyphenyl-N'—3,5-dichlorophenylurea |
| 58 | N—(3-chloro-1-methylpropyl)-aniline | 3-Chlorophenyl isocyanate | N—(3-chloro-1-methylpropyl)-N—phenyl-N'—3-chlorophenylurea |
| 59 | N—(3-chloro-3-methylpropyl)-aniline | 3-Trifluoromethylphenyl isocyanate | N—(3-chloro-3-methylpropyl)-N—phenyl-N'—3-trifluoromethylphenylurea |
| 60 | N—(3-chloro-1-methylpropyl)-aniline | 3,5-Dichlorophenyl isocyanate | N—(3-chloro-1-methylpropyl)-N—phenyl-N'—3,5-dichlorophenylurea |
| 61 | N—(3-bromo-2-methylpropyl)-aniline | 3-Trifluoromethylphenyl isocyanate | N—(3-bromo-2-methylpropyl)-N—phenyl-N'—3-trifluoromethylphenylurea |
| 62 | N—(3-bromo-2-methylpropyl)-2-methoxyaniline | 3-Trifluoromethylphenyl isocyanate | N—(3-bromo-2-methylpropyl)-N—2-methoxyphenyl-N'—3-trifluoromethylphenylurea |

It will be understood that the specification and examples are illustrative but not limitative of the present invention and that other embodiments within the spirit and scope of the invention will suggest themselves to those skilled in the art.

I claim:

1. A methyl-substituted tetrahydro-2-pyrimidinone of the formula

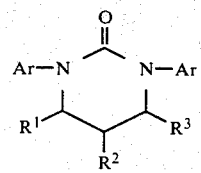

in which

Ar each independently is a phenyl or α-naphthyl group optionally substituted by at least one substituent selected from halogen, $C_1$ to $C_6$ alkyl, $C_1$ to $C_6$ alkoxy, $C_1$ to $C_6$ akylthio, nitro, phenoxy and trifluoromethyl, and $R^1$, $R^2$ and $R^3$ each independently is a hydrogen atom or a methyl group, at least one of $R^1$, $R^2$ and $R^3$ being a methyl group.

2. A compound according to claim 1 in which Ar is a phenyl or α-naphthyl group optionally substituted by at least one substituent selected from fluorine, chlorine, bromine, iodine, methyl, ethyl, propyl, isopropyl, N-butyl, isobutyl, sec.-butyl, tert.-butyl, methoxy, ethoxy, propoxy, isopropoxy, n-butoxy, isobutoxy, sec.-butoxy, tert.-butoxy, methylthio, ethylthio, propylthio, isopropylthio, n-butylthio, isobutylthio, sec.-butylthio, tert.-butylthio, nitro, phenoxy and trifluoromethyl.

3. A compound according to claim 1, in which at least one of the radicals Ar carries a substituent in the meta position.

4. A compound according to claim 1, wherein such compound is 1-(3-chlorophenyl)-5-methyl-3-phenyltetrahydro-2-pyrimidinone of the formula

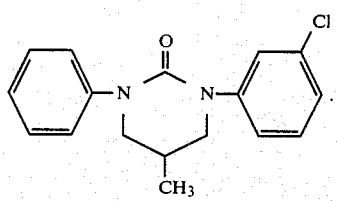

5. A compound according to claim 1, wherein such compound is 5-methyl-1-phenyl-3-(3-trifluoromethylphenyl)-tetrahydro-2-pyrimidinone of the formula

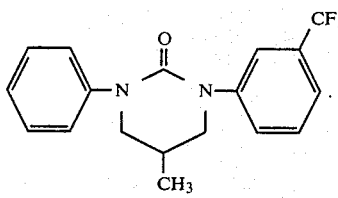

6. A compound according to claim 1, wherein such compound is 1-(3-chlorophenyl)-3-(2-methoxyphenyl)-5-methyl-tetrahydro-2-pyrimidinone of the formula

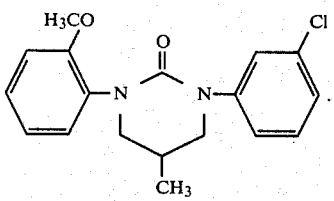

7. A compound according to claim 1, wherein such compound is 1-(2-methoxyphenyl)-5-methyl-3-(3-trifluoromethyl-phenyl)-tetrahydro-2-pyrimidinone of the formula

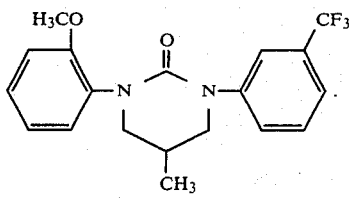

8. A compound according to claim 1, wherein such compound is 1-(3-methoxyphenyl)-5-methyl-3-phenyl-tetrahydro-2-pyrimidinone of the formula

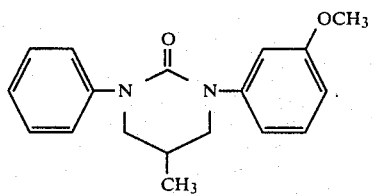

9. A compound according to claim 1, wherein such compound is 5-methyl-1-(3-methylthiophenyl)-3-phenyl-tetrahydro-2-pyrimidinone of the formula

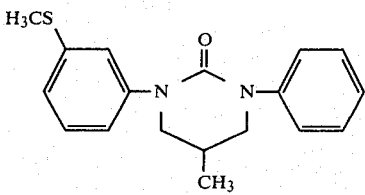

10. A herbicidal composition comprising a herbicidally effective amount of a compound according to claim 1 in admixture with a diluent.

11. A method of combating weeds comprising applying to the weeds, or to a habitat thereof, a herbicidally effective amount of a compound according to claim 1.

12. The method according to claim 11, wherein such compound is
1-(3-chlorophenyl)-5-methyl-3-phenyl-tetrahydro-2-pyrimidinone,
5-methyl-1-phenyl-3-(3-trifluoromethyl-phenyl)-tetrahydro-2-pyrimidinone,
1-(3-chlorophenyl)-3-(2-methoxyphenyl)-5-methyl-tetrahydro-2-pyrimidinone,
1-(2-methoxyphenyl)-5-methyl-3-(3-trifluoromethyl-phenyl)-tetrahydro-2-pyrimidinone,
1-(3-methoxyphenyl)-5-methyl-3-phenyl-tetrahydro-2-pyrimidinone or
5-methyl-1-(3-methylthiophenyl)-3-phenyl-tetrahydro-2-pyrimidinone.

* * * * *